(12) United States Patent
Stinson

(10) Patent No.: US 7,814,932 B2
(45) Date of Patent: Oct. 19, 2010

(54) DIGITAL PRESSURE GAUGE

(76) Inventor: David Stinson, 121 Granton Dr., Unit 21, Richmond Hill, Ontario (CA) L4B 3N4

( * ) Notice: Subject to any disclaimer, the term of this patent is extended or adjusted under 35 U.S.C. 154(b) by 864 days.

(21) Appl. No.: 10/714,624

(22) Filed: Nov. 18, 2003

(65) Prior Publication Data
US 2004/0118460 A1    Jun. 24, 2004

Related U.S. Application Data

(63) Continuation-in-part of application No. 10/248,094, filed on Dec. 18, 2002, now Pat. No. 6,960,190.

(51) Int. Cl.
*F16K 37/00* (2006.01)
(52) U.S. Cl. .................... 137/557; 137/78.1; 73/700
(58) Field of Classification Search ............... 137/557, 137/554, 552, 78.1, 78.3; 128/202.12; 73/700, 73/714, 716, 736, 753; 340/442
See application file for complete search history.

(56) References Cited

U.S. PATENT DOCUMENTS

| | | | |
|---|---|---|---|
| 3,768,820 A * | 10/1973 | Yew | 280/6.159 |
| 4,333,490 A * | 6/1982 | Enter, Sr. | 137/78.3 |
| 5,032,287 A * | 7/1991 | Salmond | 210/737 |
| 5,092,326 A * | 3/1992 | Winn et al. | 128/205.13 |
| 5,419,768 A * | 5/1995 | Kayser | 604/119 |
| 5,606,123 A * | 2/1997 | Rabizadeh | 73/146.8 |
| 5,850,833 A * | 12/1998 | Kotliar | 128/202.12 |
| 5,889,464 A * | 3/1999 | Huang | 73/146.5 |
| 6,007,330 A * | 12/1999 | Gauthier | 432/47 |
| 6,123,093 A * | 9/2000 | D'Antonio et al. | 137/78.3 |
| 6,171,104 B1 * | 1/2001 | Saito et al. | 432/18 |
| 6,518,875 B2 * | 2/2003 | DeZorzi | 340/442 |

* cited by examiner

*Primary Examiner*—John Rivell
*Assistant Examiner*—Craig Price

(57) ABSTRACT

A vacuum pressure regulator system for use in association with a vacuum system in which a vacuum is employed for healthcare purposes, for assisting in monitoring and regulating the vacuum pressure, and having a manual pressure control valve to adjust the treatment vacuum pressure supplied to the patient, a vacuum pressure sensor to sense the treatment vacuum pressure for the patient in the system, and producing a treatment vacuum pressure signal, a sampling circuit which intermittently samples the pressure signal generated by the pressure sensor and generate sampling signals, an electrically powered pressure display circuit, and digital pressure display, for receiving the sampling signals and providing a visible display, and, a non-mains power supply.

15 Claims, 5 Drawing Sheets

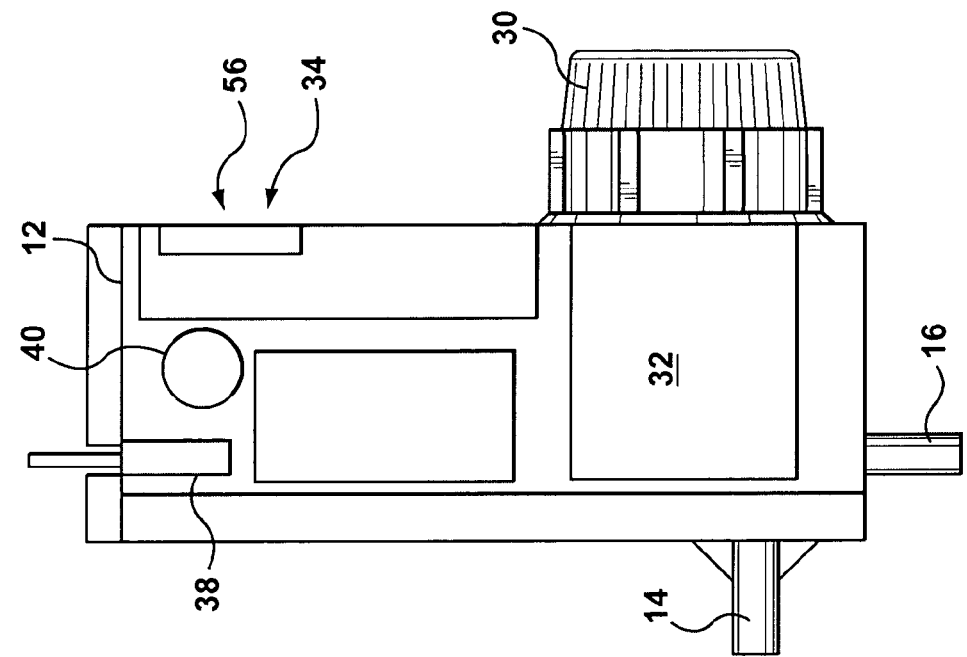
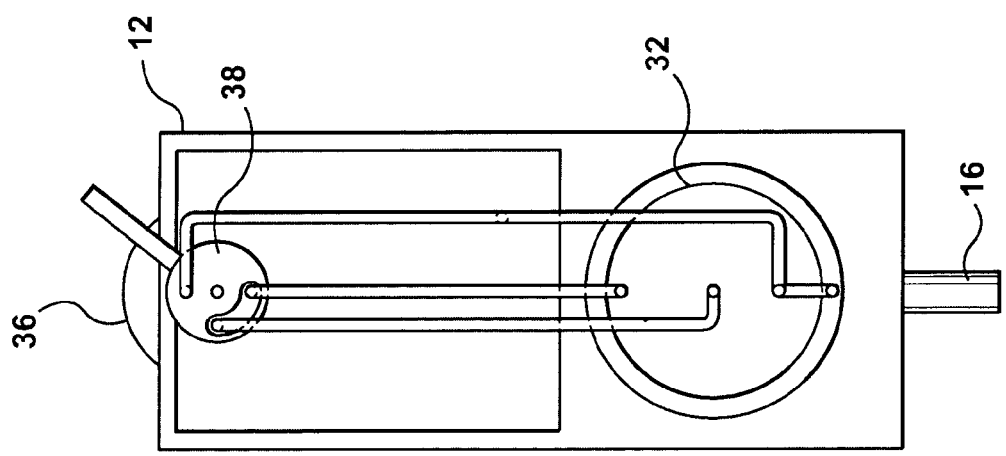

DIGITAL PRESSURE GAUGE

This application is a continuation in part of U.S. patent application Ser. No. 10/248,094 filed Dec. 18, 2002 now U.S. Pat. No. 6,960,190.

FIELD OF THE INVENTION

The invention relates to medical and hospital healthcare vacuum systems and in particular to a vacuum pressure gauge and regulator having a solid state, non-mains powered sensor for monitoring the vacuum pressure and enabling the operator to maintain a stable level of vacuum for administration to a patient, and to a vacuum regulator incorporating such a vacuum pressure gauge.

BACKGROUND OF THE INVENTION

In the field of health care, vacuum systems are required in many circumstances. A vacuum may be required to be applied to a patient for a variety of reasons.

In these cases care must be taken to ensure that the level of vacuum negative pressure is maintained at the level required for a particular treatment. To do this manual controls, known as vacuum regulators, are provided by which the level of vacuum pressure can be controlled and varied.

Pressure gauges are also provided either incorporated in or matched with the vacuum regulator, which monitor the level of vacuum pressure.

In the past the mechanical systems in such vacuum regulators for actually varying and controlling the vacuum used simple vent valves and the like. Such valves could be controlled manually usually by a control knob. The pressure gauge was usually a mechanical type gauge, which consisted of a pressure sensor with a dial, and a needle showing the pressure. An operator would glance at the dial and needle from time to time to ensure that the vacuum level remained stable at the desired pressure.

Such known pressure gauge systems have been somewhat primitive.

Usually known vacuum regulators used a simple mechanical type pressure gauge with a needle type readout dial showing the pressure. An operator would monitor the gauge reading and might adjust the manual pressure control as desired. This system was somewhat old fashioned for the hospital environment, and was not always practical in emergency situations for example in a paramedic environment, at an accident scene for example, or in an ambulance. For example the needle dial and may require to be checked repeatedly, and it was possible for the paramedic to misread the dial. An example of a needle dial type readout is shown in U.S. Pat. No. 4,915,132 where the needle dial is removably securable to a round post. The dial is sealed against leakage by "O" rings.

Such known systems were also capable of providing for intermittent vacuum pulses to be supplied at intervals as shown for example in U.S. Pat. No. 5,599,308. The intermittent control in many cases, was difficult to maintain and difficult to regulate as to timing.

U.S. Pat. No. 4,988,336 issued on Jan. 29, 1991, to G S Kohn, and discloses a complex vacuum pressure regulator in which the vacuum source is used to drive a rotary air powered motor which in turn drives an electrical generator, which is part of the regulator. The vacuum control valve is electrically operated and turns the vacuum on and off for intermittent supply of vacuum to the patient. This system is unnecessarily complex in that it incorporates its own electrical generator, and uses that generator to power the electronic on/off switching of the vacuum.

U.S. Pat. No. 5,419,768 issued on May 30, 1995, to J. P. Kayser and discloses a vacuum regulator in which the actual vacuum control valve is operated by a solenoid. The solenoid is programmed to open and close the valve automatically for intermittent operation. This system is also complex, and would consume a considerable power supply.

There is a need for a vacuum pressure regulator having a more precise pressure readout, preferably one that provides a better visual readout, such as could be provided by a digital numeral LCD display.

Preferably such a system will be independent of mains power (i.e. connected to wiring in a building), and will be a system that is solid state operated, with battery power, for most applications, thus permitting it to be used anywhere in a facility or in the field if needed.

Preferably the vacuum pressure display will be incorporated in the body of a manual vacuum pressure regulator, so that the digital vacuum pressure display is provided in a single compact unit.

Preferably there will also be an alarm, of some form, incorporated in the pressure gauge which will alert the attendant if there is a loss of vacuum.

Preferably the pressure regulator will be designed to operate on a minimum of power, so that it can be powered by a long life battery, a rechargeable battery, a 12-volt battery, or by solar power if desired. Mains power connections could also be incorporated, so as to be available to be used, when required, as an optional alternative supply.

The regulator control will preferably incorporate a potentiometer connected to the logic so that when the control knob is rotated to adjust the pressure, the sampling rate is increased temporarily. This will give an instantaneous readout, on the display of the new pressure.

BRIEF SUMMARY OF THE INVENTION

It is an aspect of this invention to provide a digital pressure display comprising a sensor for sensing a pressure, a microprocessor for intermittently enabling said sensor to sense said pressure and generate a signal, a power source, so as to generate a digital pressure reading.

With a view to providing the foregoing advantages the invention comprises a vacuum pressure regulator system for use in association with a vacuum system in which a vacuum is employed for healthcare purposes, for assisting in monitoring and regulating the vacuum pressure, and which vacuum pressure regulator system has a manual pressure control valve operable by an operator to adjust the treatment vacuum pressure supplied to the patient, a vacuum pressure sensor operable to sense the treatment vacuum pressure for the patient in the system, and to produce a treatment vacuum pressure signal, a sampling circuit operable intermittently by electrical power to sample said pressure signal generated by said pressure sensor at predetermined time intervals and generate sampling signals, an electrically powered pressure display circuit, and digital pressure display, for receiving said sampling signals and generating a visible digital pressure display, and, a non-mains power supply connected for supplying power both to said sampling circuit for sampling said vacuum sensor, and to said display circuit and said digital display.

The invention further seeks to provide such a vacuum pressure regulator including a no-pressure signal generator for generating at least one no-pressure signal representing an absence of treatment vacuum pressure, and an alarm signal generator, and an alarm responsive thereto, operable in response to a no-pressure signal to generate an alarm.

The invention further provides such a vacuum pressure regulator system in which said regulator is manually operable to adjust said treatment vacuum pressure so as to maintain a desired level of vacuum pressure.

The invention further provides such a vacuum pressure gauge system in which said no-pressure signal generator responds to the occlusion of a treatment device connected to a patient and signals an alarm.

The invention further provides such a vacuum pressure regulator system in which an operator override control is provided whereby an operator can manually override said pressure control valve and supply full vacuum for treatment of said patient.

The vacuum applied to the patient may be and usually is, connected to the patient through a know collection bottle, and material removed from the patient may be allowed to collect in such a collection bottle thus preventing the material from being withdrawn up into the vacuum system itself.

The invention also provides a method of supplying and regulating a vacuum to a patient, with a non-mains powered regulator, and sampling the vacuum pressure at timed intervals so as to conserve power.

The various features of novelty which characterize the invention are pointed out with more particularity in the claims annexed to and forming a part of this disclosure. For a better understanding of the invention, its operating advantages and specific objects attained by its use, reference should be made to the accompanying drawings and descriptive matter in which there are illustrated and described preferred embodiments of the invention.

IN THE DRAWINGS

FIG. 2 is a sectional illustration of a vacuum pressure regulator of FIG. 1 along line 2-2 of FIG. 1.

FIG. 3 is a conduit diagram illustrating the layout of the various conduits connecting the components of the pressure regulator of FIG. 1.

DETAILED DESCRIPTION OF THE INVENTION

The invention to be described herein is in one embodiment described in relation to air and a vacuum. However, the invention is applicable to any gas with the appropriate selection of materials. Furthermore, the invention can be used with fluids. Moreover, the invention can be used for both positive and negative pressures.

Figure 1:
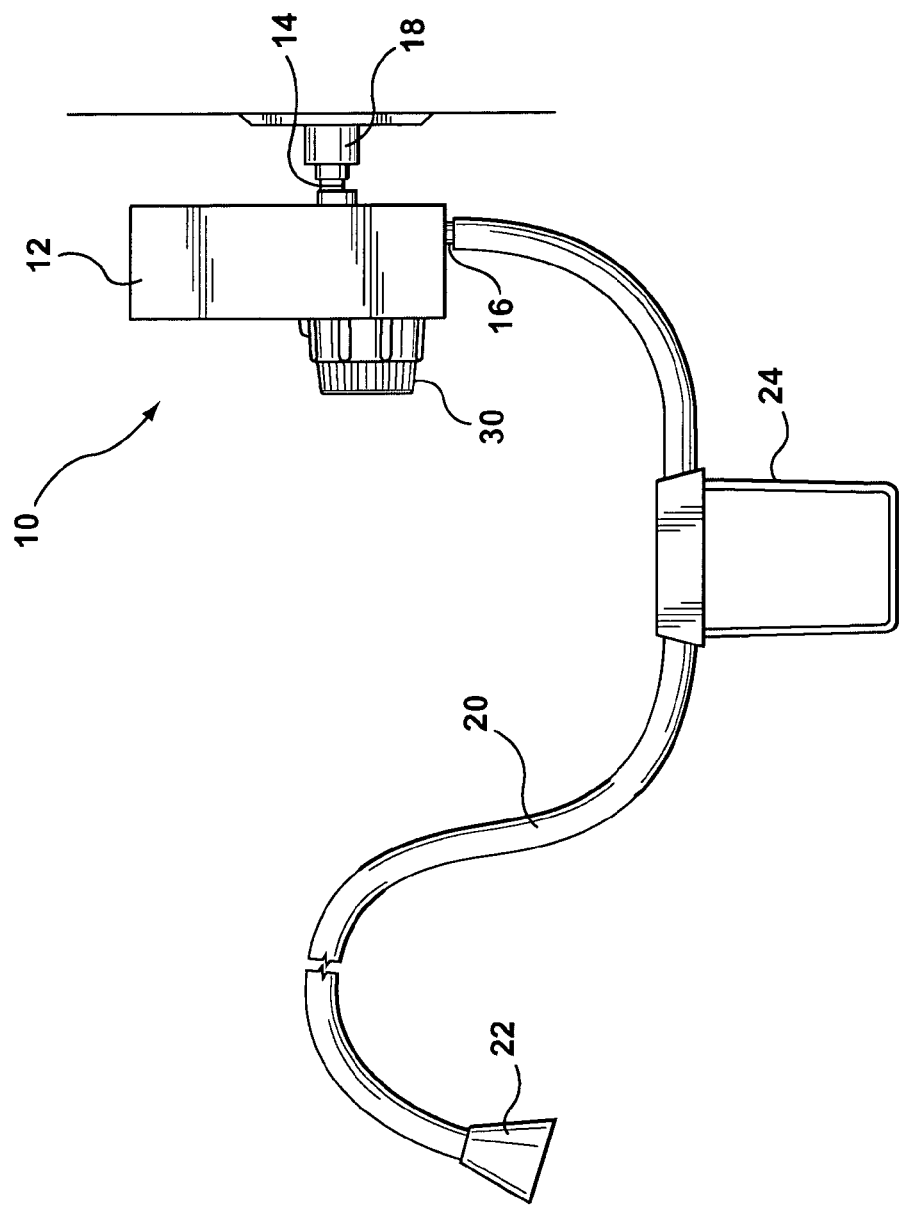
FIG. 1 is a schematic view of a vacuum pressure system, showing the vacuum pressure regulator illustrating the invention.

Referring to FIG. 1 it will be seen that the invention is there illustrated in the form of a vacuum regulator 10 having a housing 12, a vacuum source connection 14, and a vacuum patient connection 16. Typically the vacuum connection 14 will be connected to a known vacuum conduit 18 common in many hospitals, and paramedical vehicles. The conduit, in a hospital is located in or on a wall, and has connection points in various rooms, by means of which a paramedic, doctor or nurse, may have quick access to a source of vacuum wherever required. The patient connection 16 may be connected by a patient hose 20 to a vacuum tube or device (not shown), by means of which the patient may be treated with a vacuum in any desired circumstances.

Typically a collector bottle 24 is provided in the patient hose, for collecting any mucous or other material removed from the patient via the hose.

Referring to FIGS. 2 and 3 the components within the vacuum regulator housing are seen in more detail. On the housing 12 there is a manually operable control knob 30, connected to a pressure control valve 32 within housing 12. By operation of knob 30 the vacuum pressure can be adjusted, manually, as desired. Knob 30 is coupled with a control sensor, in this case a potentiometer ring 31 known per se (FIG. 4), for reasons described below.

The vacuum regulator 10 has a visual indicator or window 34 for a display (described below), on which the treatment vacuum pressure is displayed, and also has an alarm 36. The alarm may be a flashing light, an audible buzzer or a combination of warning alert devices.

A mode select switch 38 is operable to select either automatic regulation or manual override, as desired.

In accordance with the invention a power source, in this case a battery 40 is located within housing 12 and is connected to a circuit board of the vacuum sensor as will be described below. Other forms of power source could replace the battery or could be combined with the battery, a rechargeable storage device, solar power, or a mains power supply and transformer.

Figure 4:
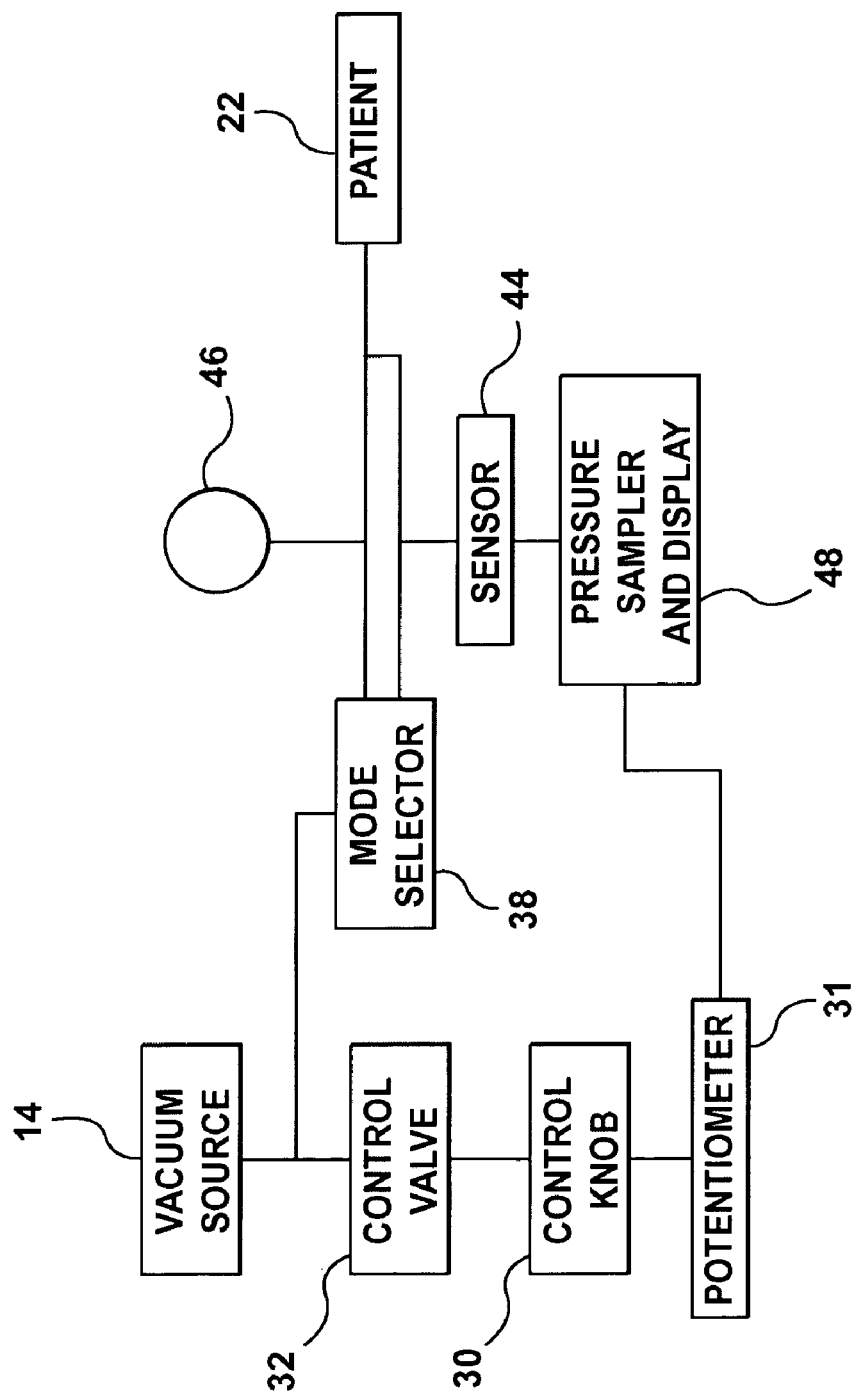
FIG. 4 is a block diagram illustrating the connection of the mechanical components of the vacuum pressure controls FIG. 1.

FIG. 4 illustrates the vacuum conduit connections within the housing 12 between the various mechanical components, corresponding to FIG. 3 but in schematic form. The vacuum source 14 is shown connected to the control valve 32. Such control valves are known, and the details are not shown for the sake of clarity. The control knob 30 connects to the control valve for manual operation and adjustment of the control valve, by an operator. This permits the operator to manually adjust the level of vacuum being supplied to the patient. The mode selection control 38 allows an operator to select either an off position or an automatic operation position, of the control valve at a selected vacuum pressure, or manual override position, which cuts out the control valve and applies full vacuum to the patient. A pressure sensor 44 senses the vacuum pressure and provides a pressure signal.

Figure 5:
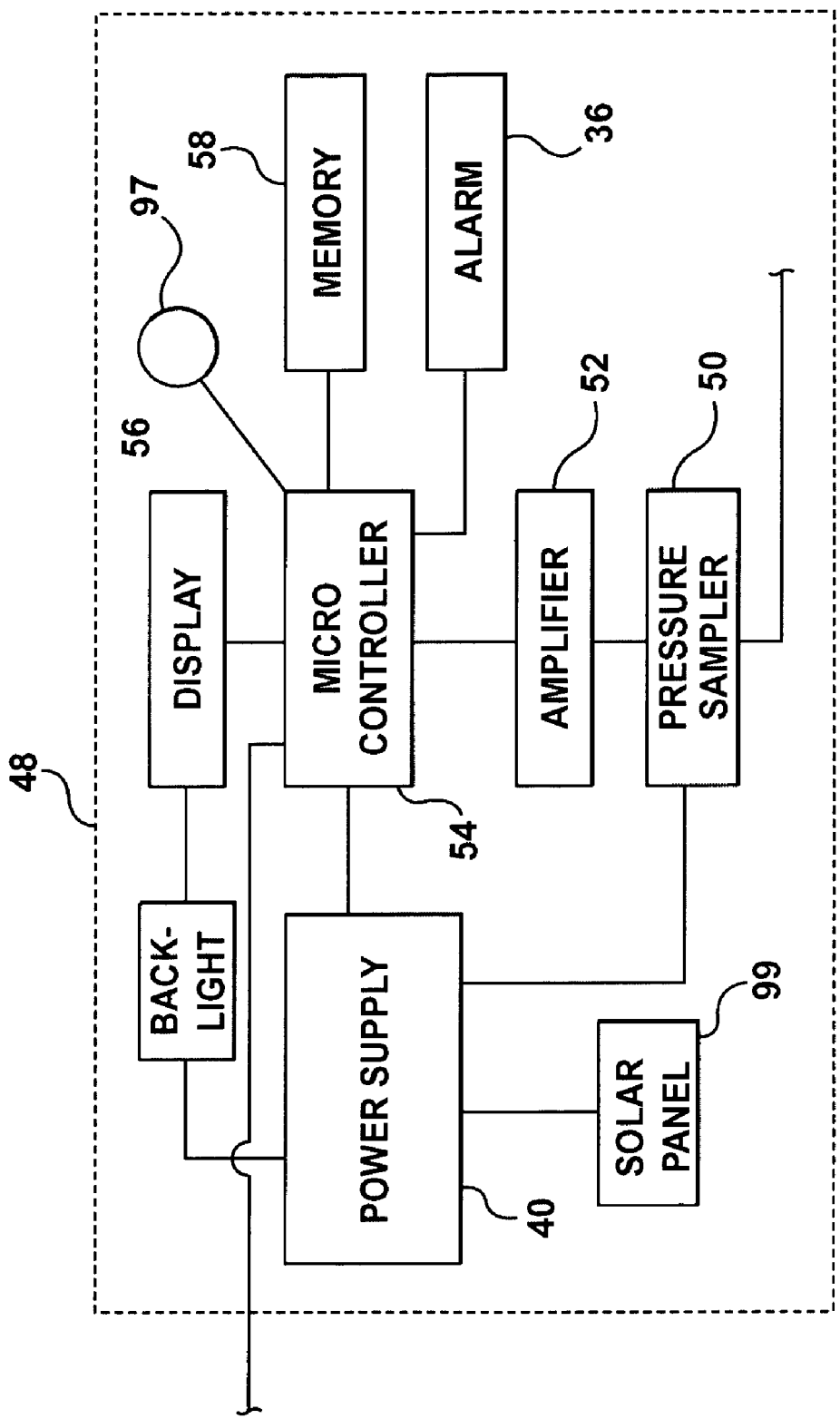
FIG. 5 is a block circuit diagram of the vacuum pressure sensor and display.

FIG. 5 illustrates the electronic circuit by which the pressure signal is sampled at intervals. A further vent 46 is provided in the line connection to the patient.

A sampler circuit 48 is located in housing 12, which is described below. A pressure sampler 50 is connected to the pressure sensor 44, and operates at intervals to sample the pressure detected in the pressure sensor. Sampler 50 is powered by power supply 40. This can be any one of, or a combination of the various different power supplies listed above.

Pressure sampler 50 is connected to amplifier 52 to amplify the pressure signal. Amplifier 52 is connected to micro controller 54. Controller 54 is connected to a digital display, typically a LCD display, shown as 56. The controller 54 is also connected to the potentiometer of control knob 30.

The controller 54 controls the sampler 50, which then samples the pressure at predetermined time intervals. This provides a read out on the display 56 each time a sample is taken. This greatly reduces the power consumption of the system. Thus a power supply in the form of a long-life battery will provide extended operation, without the need for a mains connection.

The sampling rate can be changed by the controller 54. Thus as the control knob 30 is rotated the controller 54 will temporarily increase the sampling rate of the sampler 50. In this way the display will give an instantaneous reading of the new pressure setting.

The micro controller 54 generally comprises an electronic chip, which has embodied therein the logic for controlling the sampler 50. The micro controller controls the time interval at which the vacuum pressure is monitored and sampled and read. The reason for sampling at intervals rather than continuously is to extend the life of the power supply such as the battery or the like. Accordingly, batteries can be used to provide DC power.

The life of the batteries can be further extended by including a light sensor 97 associated with the digital display 56 and part of the circuitry that would sense when light would be present in the vicinity of the vacuum regulator in which case the sampler circuit 48 would continue to intermittently sample the vacuum pressure as previously described. However, whenever it was dark (for example at night or the unit in a package) or whenever the room was exposed to a selected low light or candle power the digital display would shut down. In other words the numeric display on the digital display would go out since it would be too dark in the room for anyone to walk around. This then saves battery power, as the LCD display for example would not be powered. However, the vacuum would still be sampled intermittently as described if the patient was on vacuum since the alarm may go off if the vacuum is blocked as previously described. Once the light was back into the room the light sensor would sense this condition and turn the digital display back on. Alternatively, the display and the intermittent sampling can be shut down, (when the room is dark) but the light sensor remains active. Once the light sensor senses light the display is powered, and the pressure sensor is intermittently sampled.

The micro controller can be programmed so that when the digital display is reactivated because it is no longer dark, or when the control knob 30 is rotated to different vacuum level the intermittent time period when the vacuum is sampled is temporarily increased, i.e. the sampling rate is increased to give a more accurate reflection of the vacuum during this transition period.

Furthermore, the regulator could carry a solar panel 99 to charge or recharge rechargeable batteries to further extend the life of the battery power. Examples of batteries that can be used include AA or 3.6 volt batteries. In one embodiment two of such batteries are used.

Moreover, although the vacuum is sampled intermittently the display will show the level of vacuum continuously. Therefore the digital display will show numerical numbers continuously which are generally easier to read more accurate and reliable than a needle dial.

A memory 58 is connected to controller 54 to store data.

Figure 6:
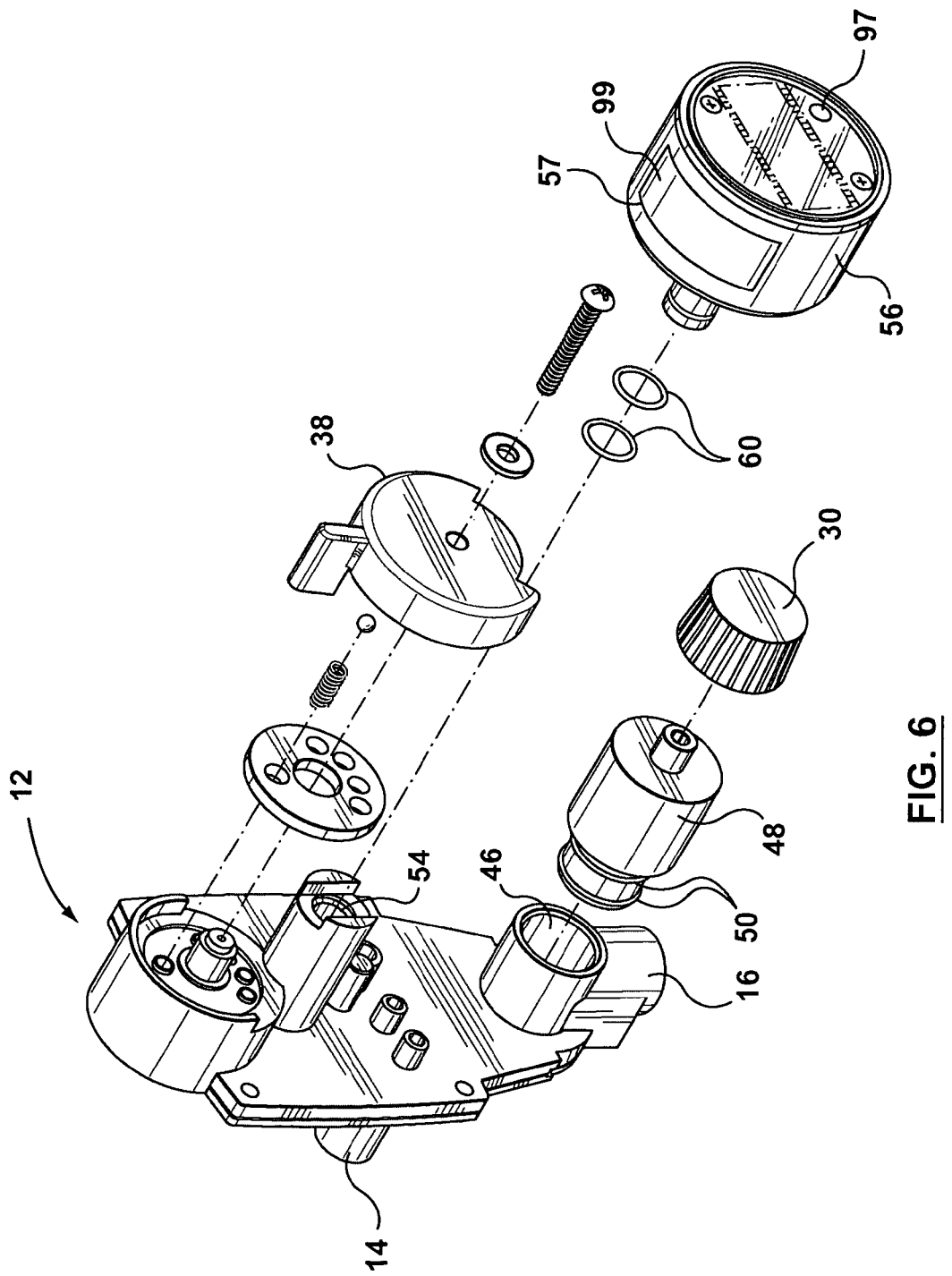
FIG. 6 is a view of another embodiment of the invention.

FIG. 6 illustrates another embodiment of the invention, which shows a vacuum regulator 12 presenting a vacuum inlet 14 and vacuum outlet 16. A selector dial 38 is utilized to select the vacuum regulator in the "Off", "Full Vacuum" or "Regulated Vacuum" modes of the vacuum regulator in a manner well known to those persons skilled in the art. A regulator 48 communicates with a regulator well in a manner well known to those persons skilled in the art. A control knob 30 is shown to adjust the level of vacuum, however, a potentiometer ring is not used in this embodiment. A digital display 56 however is shown.

The digital display 56 is adapted to engage an aperture 54 of hollow flange 56.

Prior art vacuum regulators show needle dials engaged with hollow flanges as illustrated in U.S. Pat. No. 4,915,132. Therefore, the digital display 56 described herein can be substituted in place of the prior art needle dials. The digital display is sealed against leakage by "O" rings 60.

In the embodiment shown in FIG. 6 the pressure sensor 44, sampler circuit 50 including the power supply 40 would be disposed or contained within the display housing 57. Furthermore, the light sensor 97 and solar panel 99 is disposed on the housing 57.

By utilising the invention described herein the life of the battery is extended. For example in one such application a one year battery has been extended to ten years.

Moreover, as a further alternative the invention described herein can include a microprocessor that may continuously enable the sensor to sense the pressure and generate a signal.

The foregoing is a description of a preferred embodiment of the invention which is given here by way of example only. The invention is not to be taken as limited to any of the specific features as described, but comprehends all such variations thereof as come within the scope of the appended claims.

I claim:

1. A digital pressure display for a vacuum regulator, the digital pressure display comprising:
   (a) sensor means for intermittently sensing said pressure;
   (b) microprocessor means to intermittently enable the operation of said sensor means to sense said pressure at predetermined sampling intervals and generate a signal; and
   (c) power means to power said sensor means and said microprocessor means for generating a digital pressure reading;
   wherein the sensor means sensing said pressure at predetermined sampling intervals reduce power requirements; and
   (d) a light sensor for sensing a dark condition so as to terminate the generation of said digital pressure reading during said dark condition, and wherein the predetermined sampling interval is changeable during adjustment of the vacuum regulator.

2. A digital pressure display as claimed in claim 1 wherein said power means comprises a battery.

3. A digital pressure display as claimed in claim 2 wherein said battery is rechargeable.

4. A digital pressure display as claimed in claim 2 including circuitry means having a solar power cell to recharge said battery.

5. A digital pressure display as claimed in claim 2 wherein said digital display is replaceable with a needle dial display.

6. A digital pressure display for a vacuum regulator, the digital pressure display comprising:
   (a) a manual pressure control valve operable by an operator to adjust a vacuum pressure;
   (b) a vacuum pressure sensor operable to sense the vacuum pressure, and to produce a pressure signal;
   (c) the operation of a sensor means intermittently enabled by a microprocessor means at predetermined sampling intervals operable to sample said pressure signal generated by said vacuum pressure sensor and generate sampling signals, the predetermined sampling interval is changeable by operation of the manual pressure control valve;
   (d) an electrically powered pressure display circuit communicating with the digital pressure display, for receiving said sampling signals and generating a visible digital pressure display; and a power means connected to said microprocessor means, said sensor means for sampling said vacuum pressure sensor, said display circuit and said digital pressure display.

7. The digital pressure display as claimed in claim 6 and including a no-pressure signal generator for generating at least one no-pressure signal representing an absence of treatment vacuum pressure, and an alarm signal generator, and an alarm responsive thereto, operable in response to a no-pressure signal to generate an alarm.

8. The digital pressure display as claimed in claim 7 and wherein said control valve is manually operable to adjust said vacuum pressure so as to maintain a desired level of vacuum pressure.

9. A digital pressure display for an adjustable pressure regulator, the digital pressure display comprising:
   (a) sensor means for intermittently sensing said pressure;
   (b) microprocessor means to intermittently enable the operation of said sensor means to sense said pressure and generate a signal at predetermined sampling intervals;
   (c) power means to power to said sensor means and said microprocessor means; and
   (d) a display means operable to display a pressure signal in response to said signal wherein the power means power said sensor means and said microprocessor means; and wherein the predetermined sampling interval is changeable during adjustment of the pressure regulator.

10. The digital pressure display as claimed in claims 6 or 9 including a controller said controller connected to said sensor means and operable to temporarily increase the rate of sampling intervals, during adjustment of the regulator.

11. A digital pressure display as claimed in claims 6 or 9 wherein said power means comprises a battery.

12. A digital pressure display as claimed in claim 11 wherein said battery is rechargeable.

13. A digital pressure display as claimed in claim 11 further including a light sensor for sensing a dark condition so as to terminate the generation of said digital pressure reading during said dark condition.

14. A digital pressure display as claimed in claim 11 further including a light sensor sensing a dark condition so as to terminate the generation of said digital pressure reading during said dark condition.

15. A digital pressure display as claimed in claim 11 including circuitry means having a solar power cell to recharge said battery.

* * * * *